(12) United States Patent
Blick

(10) Patent No.: US 8,696,881 B2
(45) Date of Patent: Apr. 15, 2014

(54) PATCH-CLAMP PROVIDING ON-CHIP THERMAL GRADIENT

(75) Inventor: Robert H. Blick, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 265 days.

(21) Appl. No.: 13/278,300

(22) Filed: Oct. 21, 2011

(65) Prior Publication Data

US 2013/0098762 A1   Apr. 25, 2013

(51) Int. Cl.
*G01N 33/487* (2006.01)

(52) U.S. Cl.
CPC ............................... *G01N 33/48728* (2013.01)
USPC .......................................... 204/408; 436/180

(58) Field of Classification Search
CPC ................................................ G01N 33/48728
USPC .......................................... 204/408; 436/180
See application file for complete search history.

(56) References Cited

U.S. PATENT DOCUMENTS

| | | | |
|---|---|---|---|
| 7,485,857 B2 | 2/2009 | Blick | |
| 2003/0180965 A1* | 9/2003 | Yobas et al. | 436/180 |
| 2010/0127716 A1 | 5/2010 | Blick et al. | |
| 2010/0129603 A1 | 5/2010 | Blick et al. | |
| 2011/0111179 A1 | 5/2011 | Blick et al. | |

OTHER PUBLICATIONS

P. Correges, et al. "A simple, low-cost and fast Peltier thermoregulation set-up for electrophysiology", Journal of Neuroscience Methods, vol. 83, No. 2, Sep. 1998, p. 177-184.*

* cited by examiner

*Primary Examiner* — J. Christopher Ball
(74) *Attorney, Agent, or Firm* — Boyle Fredrickson, S.C.

(57) ABSTRACT

A patch clamp system providing precise and rapid temperature control of constrained cell membranes employs the thermal element attached to the substrate of the patch clamp. In one embodiment, the thermal element is a Peltier device fabricated on a silicon membrane wafer bonded to the substrate of the patch clamp.

19 Claims, 4 Drawing Sheets

PATCH-CLAMP PROVIDING ON-CHIP THERMAL GRADIENT

STATEMENT REGARDING FEDERALLY SPONSORED RESEARCH OR DEVELOPMENT

This invention was made with government support under FA9550-08-1-0337 awarded by the USAF/AFOSR. The government has certain rights in the invention.

CROSS REFERENCE TO RELATED APPLICATION

--

BACKGROUND OF THE INVENTION

The present invention relates to electrophysiology and in particular to "patch clamping" for investigating ionic and molecular transport through cellular membranes via ion channels and pores. Invention permits construction of microscale pores that may be readily sealed to cellular membranes and controlled in temperature with respect to the surrounding liquid bath.

Ion channel investigation using patch clamps plays an important role in drug discovery and preliminary drug screening or evaluation, for example, by providing a model that shows an effect of a drug on ion channels. Experiments performed with patch clamps can be used to test for adverse effects or search for positive therapeutic effect in the treatment of ion channel related diseases.

Drug screening can require a large number of ion channel measurements. In current practice, planar patch clamps are preferable because they allow parallelization of multiple samples on a substrate, often referred to as a wafer, chip, or well-plate, and facilitate measurement automation. Each sample includes a cell or cell wall that is positioned so that an ion channel in the cell or cell wall is aligned with a pore at the sample site. The cell or cell wall is sealed to the patch clamp substrate in a manner that allows ion channel investigations with only a small amount of electrical current, possible because of a high resistance seal between the patch clamp substrate and the cell wall (a gigaohm seal or gigaseal). Gigaohm seals achieved using on-chip patch clamp procedures usually have electrical resistance values of about one gigaohm, with resistance values of up to about 5 gigaohms being achieved in some instances.

Planar patch clamp substrates can be made from, for example, silicon (and other semiconductors), Teflon®, PDMS (polydimethylsiloxane), PSG (phosphosilicate glass), or glass. While such materials prove suitable for many planar patch clamp implementations, a single crystal quartz (quartz) material can be particularly desirable for making planar patch clamp substrates. Quartz exhibits particularly high electrical insulating properties and is piezoelectric.

Traditionally, micromachining of glass and quartz is performed using a combination of lithography and reactive ion etching (RIE). However, RIE techniques require multiple steps and are relatively slow processes. US patent application 2011/0111179 entitled: "Laser Drilling Technique for Creating Nanoscale Holes" and US patent application 2010/0129603 entitled: "Retro-Percussive Technique for Creating Nanoscale Holes", both assigned to the assignee of the present invention and hereby incorporated by reference, teach improved methods for micro-machining small holes (e.g. 1 µm and below) in a substrate for patch clamps and other purposes, the holes providing desirable shape and smoothness for creating gigaohm seals with cells.

At times it may be desirable to investigate temperature gradients around the patch clamp. This may be done by changing the temperature of the water bath in which the cells are held.

SUMMARY OF THE INVENTION

The present invention provides an improved method of controlling temperature of a cell or portion of a cell held in the patch clamp by integrating a thermoelectric element with the substrate closely proximate to the cell region. In one embodiment, the thermoelectric device is a thin semiconductor wafer that may be bonded to the substrate having the cell stabilizing pores.

Specifically, the present invention provides a patch clamp chip for electrophysiology having a substrate with an outer surface and a hole extending through the substrate and opening at the first outer surface to provide a location adapted for immobilization of a cell membrane in an electrically sealing attachment against the opening. A thermal element is fixed to the outer surface of the substrate proximate to the opening and adapted to heat a cell membrane positioned on the opening according to a received electrical signal.

It is thus a feature of at least one embodiment of the invention to provide localized temperature control of cell membranes for temperature-based experiments. By eliminating the delay attendant to affecting the cell membrane through the heating of surrounding fluid, more precise temperature control may be had. The invention may permit a temperature gradient to be established either between cis- ("on the same side") or trans- ("on opposite sides") solutions defined across the cell membrane.

The substrate may be an insulating material.

It is thus a feature of at least one embodiment of the invention to provide a local heating for desirable substrate materials that do not conduct electricity.

The substrate may be selected from the group consisting of glasses and quartz. The hole may be less than 1000 nanometers in diameter.

It is thus a feature of at least one embodiment of the invention to provide a method of speeding substrates that are amenable to laser drilling of extremely small holes.

The thermal element may be a Peltier device positioned on the opening.

It is thus a feature of at least one embodiment of the invention to provide for both active heating and cooling of the cell for more precise control and a wider range of possible experiments.

The Peltier device may be a semiconducting membrane having n- and p-doped regions.

It is thus a feature of at least one embodiment of the invention to provide a simple method of fabricating an integrated Peltier device readily attached to a patch clamp chip surface.

The semiconductor membrane may be less than 100 micrometers in thickness.

It is thus a feature of at least one embodiment of the invention to provide a low mass thermal element for rapid temperature response. It is a feature of at least one embodiment of the invention to provide a thermal element that may be readily wafer bonded to another substrate.

The opening may provide an outward flaring crater at the outer surface. The opening may have a surface finish suitable for establishing a gigaohm seal with a cell membrane.

It is thus a feature of at least one embodiment of the invention to provide a thermal element that works with laser "retro-percussive" drilling systems providing a desirable surface finish for engagement of cell membranes.

These particular objects and advantages may apply to only some embodiments falling within the claims and thus do not define the scope of the invention.

DETAILED DESCRIPTION OF THE PREFERRED EMBODIMENT

Figure 1:
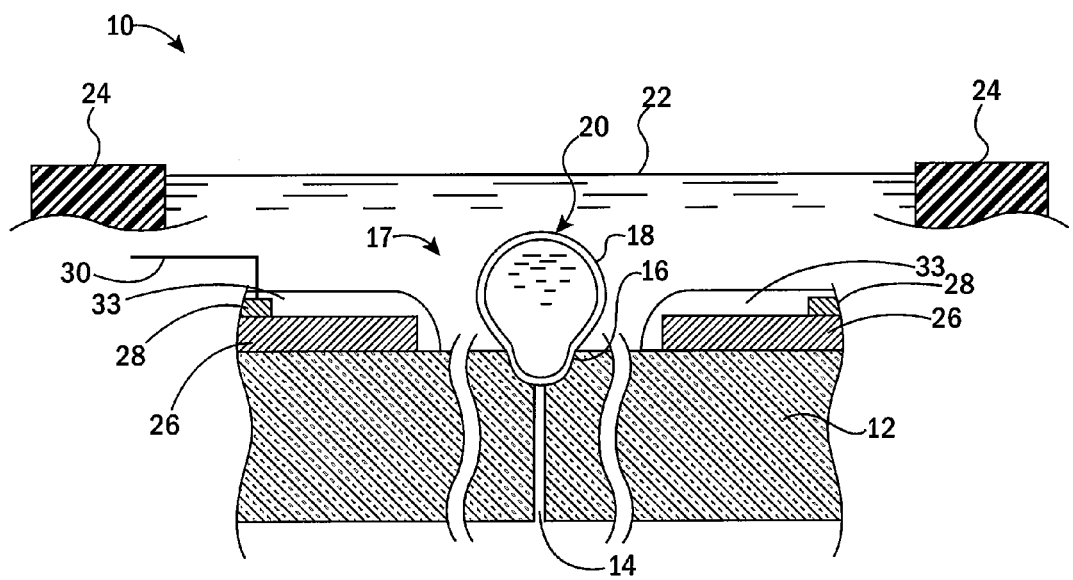
FIG. 1 is a simplified cross-sectional representation of a patch clamp sample site constructed according to the present invention showing a cell membrane immobilized on an opening through insulating substrate and surrounded by a thermal element for establishing a temperature gradient affecting the cell membrane.

Referring now to FIG. 1, a patch clamp assembly 10 of the present invention may provide an insulating substrate 12, for example, a glass or quartz material having a pore 14 extending vertically through the substrate 12 from a lower surface of the insulating substrate 12 to a shallow bowl-shaped opening 16 at the upper surface of the insulating substrate 12.

The opening 16 may have a smooth "fire polished" surface providing a gigaohm electrical seal with a cell membrane 18 of a biological cell 20. The biological cell 20 may be immobilized at the opening 16, for example, by differential pressure across the upper and lower surfaces of the substrate 12.

Generally the upper surface of the substrate 12 will be in contact with a liquid 22 providing a compatible environment for the cell 20 and/or the cell membrane 18. The liquid 22 may be retained within a well having walls 24 formed, for example, of an insulating polymer material such as PDMS molded thereto. Electrodes (not shown) may communicate with the liquid 22 and with the interior of the cell 20, for example, through the electrode inserted through pore 14 or with a liquid layer below the substrate 12 according to many variations understood in the art, to major electrical characteristics of the cell membrane.

An electrically controllable thermal element 26 may be attached to the upper surface of the substrate 12 around the opening 16 which is exposed through an aperture 17 in the thermal element 26. The thermal element 26 may provide control of the local thermal environment of the cell 20 at opening 16 by means of control of an electrical current passed into the thermal element 26 through contacts 28 attached to the same, the latter communicating with remote power source 30. The thermal element 26 may be covered with an insulating coating 33 to protect it from the liquid 22.

In one embodiment, the thermal element 26 may be a Peltier device, such devices allowing the local thermal environment about the opening 16 to be heated or cooled depending on the polarity of electrical current applied to the contacts 28 as is generally understood in the art. The thermal element 26 may alternatively be a thin-film resistive element providing for resistive heating only.

Generally the diameter opening 16 and the pore 14 will be less than 1000 nanometers to be consistent with dimensions of the cell 20. The aperture 17 in the thermal element 26 about the opening 16 will be larger but such that the edge of the thermal element 26 is proximate to the opening 16 to ensure good thermal communication between the thermal element 26 and the opening 16 and reduce thermal loss into the substrate 12 and thermal delay to the opening 16.

Figure 2:
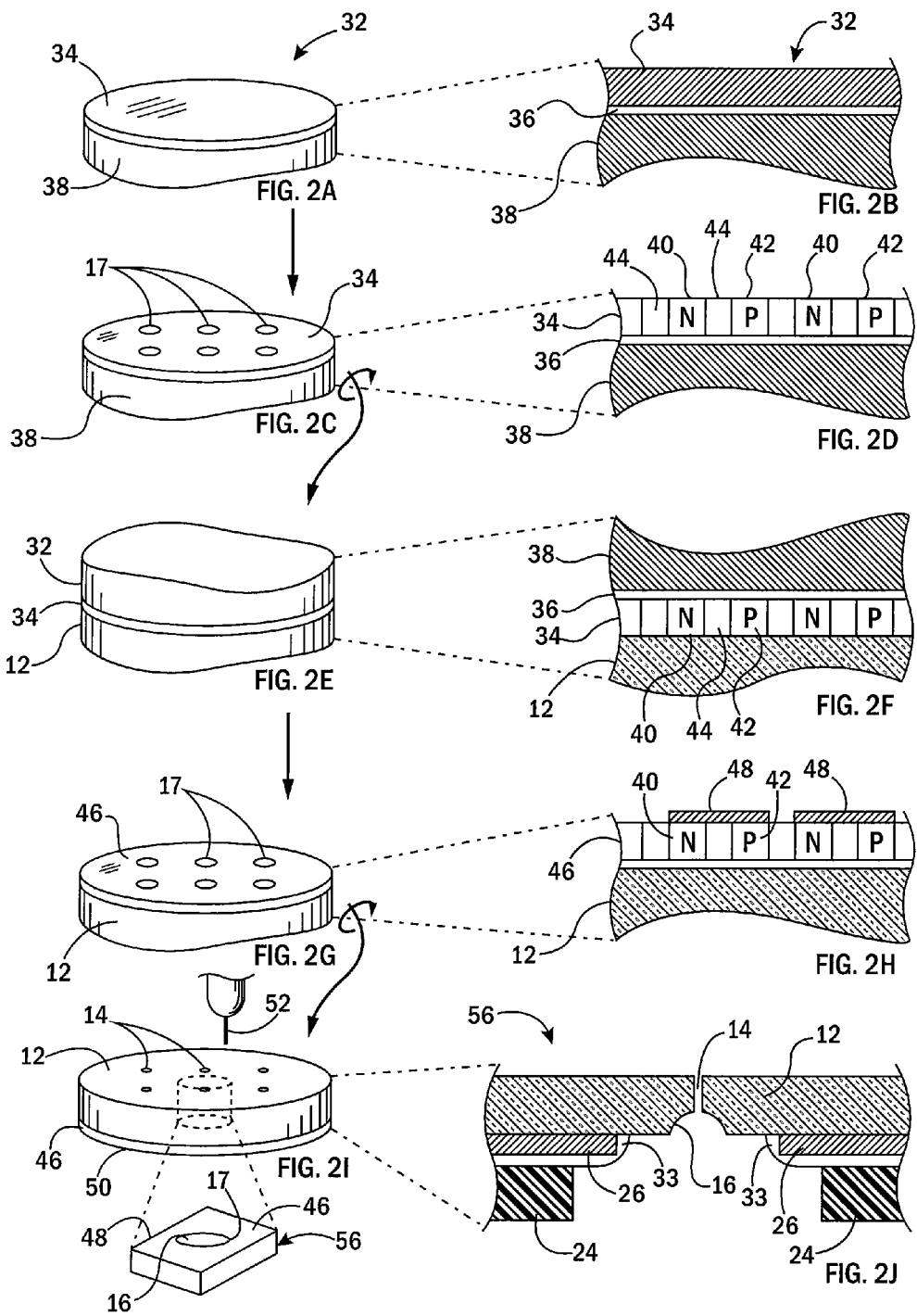
FIGS. 2A-2J are a set of corresponding perspective and cross-sectional fragmentary views of the components of the patch clamp of FIG. 1 during fabrication according to one fabrication method in which a Peltier device formed on a silicon membrane is wafer bonded to an insulating substrate.

Referring now to FIGS. 2a and 2b, in one embodiment, the thermal element 26 is fabricated on a silicon wafer and, in particular, an SOI wafer 32 of a type widely used in the integrated circuit industry. Such an SOI wafer 32 provides a monocrystalline upper silicon layer 34 on top of an insulating oxide layer 36, the latter supported by a bulk silicon substrate 38. SOI wafers 32 may be manufactured by a variety of processes, for example by ion beam implantation of oxygen into a single crystal silicon substrate to form a buried oxide layer. Alternatively, the SOI wafer 32 may be created by bonding a second silicon wafer to the silicon substrate 38 by means of the oxide layer 36. The second silicon wafer is then reduced in thickness to produce the upper monocrystalline silicon layer 34. SOI wafers 32 may also be produced by growing a silicon crystal directly on the oxide layer 36 prepared with an appropriate template for homoepitaxy.

The upper monocrystalline silicon layer 34 of the SOI wafer 32 may be thinned to the desired thickness of thermal element 26 by using the so-called "Smart Cut" method in which the upper monocrystalline silicon layer 34 is fractured along a line of bubbles near the oxide layer 86, the bubbles created by hydrogen implantation. This technique is described generally in U.S. Pat. No. 6,372,609 to Aga et al. entitled: Method of Fabricating SOI Wafer by Hydrogen Ion Delamination Method and SOI Wafer Fabricated by the Method, issued Apr. 16, 2002 and hereby incorporated by reference. Thinning of the upper monocrystalline silicon layer 34 may alternatively be done by oxidation of the exposed surface of the upper monocrystalline silicon layer 34 to create silicon dioxide and the eroding of the silicon dioxide layer with hydrofluoric acid. About 2.5 nm of silicon may be removed per cycle. Alternatively, the upper monocrystalline silicon layer 34 of the SOI wafer 32 may be mechanically ground and polished.

Referring to FIG. 2C, the upper silicon layer 34 may then be selectively attached to produce apertures 17 in the form of holes through the upper silicon layer 34 extending down to the oxide layer 36 as shown in FIG. 2D. These apertures 17 may be produced, for example, using a resist and etchant technique or the like.

Referring now to FIG. 2D, successive resist masks may be used to provide a series of adjacent n-doped regions 40 and p-doped regions 42 extending into the upper silicon layer 34 to the oxide layer 36. This doping may be implemented by standard integrated circuit techniques in which a suitable masking material is applied to the upper surface of the upper silicon layer 34 and doping material implanted, for example, by ion beam. Alternatively, properly doped high Seebeck materials such as PbTe may be deposited by plasma vapor deposition sputtering or chemical vapor deposition or other process into this region 40. Alternately, doping materials may be deposited on the surface and thermally diffused to form an alloy. These materials will then be coated by Parylene or the like to prevent poisoning of the biological materials.

Undoped substantially insulating (semiconducting) portions 44 may be left between the regions 40 and 42.

Referring now to FIGS. 2E and 2F, the wafer 32 next may be inverted and its now lower surface bonded to the upper surface of an insulating substrate 12 using a wafer bonding technique, for example, as described in: H. S. Kim, R. H. Blick, D. M. Kim, C. B. Eom, "Bonding silicon-on-insulator to glass wafers for integrated bio-electronic circuits", Applied Physics Letters 85, 2370 (2004), hereby incorporated by reference in its entirety.

Referring now to FIG. 2G, the now upper surface to the facing silicon substrate 38 and oxide layer 36 may then be removed revealing the apertures 17 of a membrane 46 formed from silicon layer 34 attached to the substrate 12. This process is also described in the above referenced paper to Kim et als.

Referring now to FIG. 2H, patterns of metallization layers 48 may then be applied to the exposed face of the membrane 46 joining the n-doped regions 40 with the p-doped regions 42 in a substantially continuous electrical series to provide a Peltier device that may provide a temperature gradient along the plane of the membrane 46 as will be described below.

Figure 3:
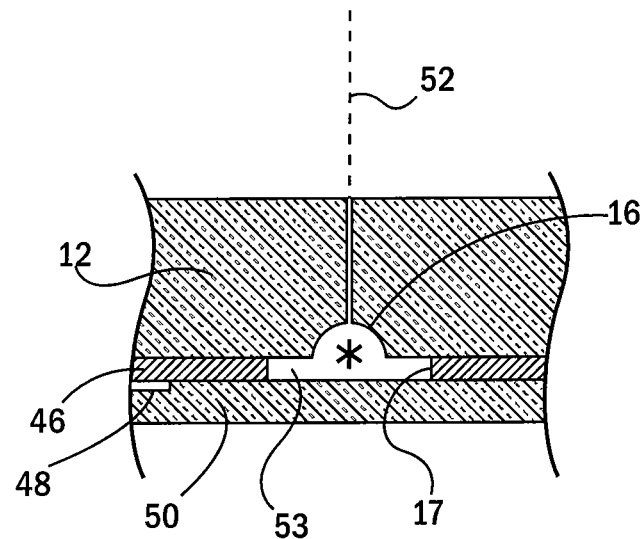
FIG. 3 is a cross-section similar to that FIG. 2H showing preparation of the combined substrate and membrane for laser hole drilling.

Referring now to FIGS. 2I and 3, the combined membrane 46 and substrate 12 may be again inverted supported on a rear surface abutting the membrane 46 by a backer layer 50. An energy absorbing material 53 may be placed between the backer layer 50 and the membrane 46. Specifically, the backer layer 50 may be a glass slide placed against the membrane 46 to trap the energy absorbing material 53 therein, the energy absorbing material 53 tailored to absorb energy from the laser beam 52. Pores 14 centered within the aperture 17 may then be produced by means of a laser induced percussive technique in which a laser beam 52 is directed downward on the exposed surface of the insulating substrate 12 to heat and produce an explosion in the energy absorbing material 53 producing a fire polished opening 16. This technique and suitable materials are described in US patent application 2011/0111179 entitled: "Laser Drilling Technique for Creating Nanoscale Holes" assigned to the assignee of the present invention and hereby incorporated by reference in its entirety. The pores 14 will have a diameter of less than 1000 nm and may have a diameter of less than 20 nm and in some embodiments less than 10 nm.

Alternatively, the drilling process described above may occur before attachment of the membrane 46 with the subsequent attachment of the membrane 46 requiring proper registration of the apertures 17 and the openings 16.

Referring again to FIG. 2I, the backer layer 50 may be removed and substrate 12 and membrane 46 may then be divided into individual die 56 by conventional integrated circuit techniques, each die 56 holding one aperture 17 and one opening 16 of membrane 46 with exposed metallization layers 48.

Referring to FIG. 2J (shown inverted to be consistent FIG. 2I), the insulating coating 33 may then be applied to the membrane 46 around the aperture 17 together with the material producing the well walls 24, the latter, for example, being a PDMS applied through molding or other similar process.

Figure 4:
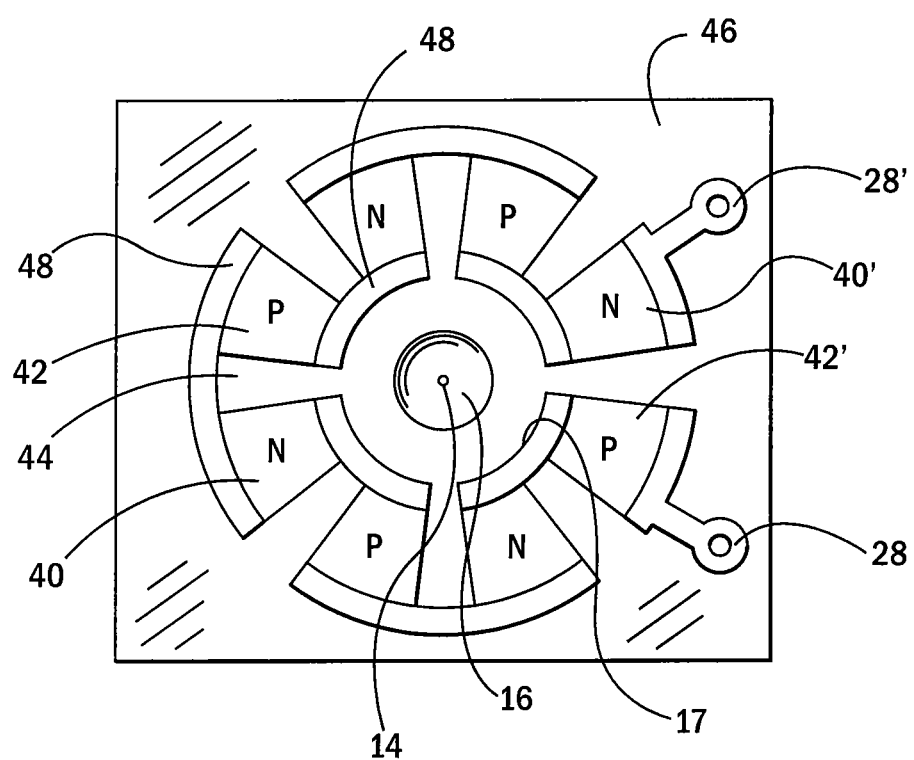
FIG. 4 is a top plan view of the patch clamp sample site of FIG. 1 showing one configuration of doped regions establishing the Peltier device providing along-plane heat gradients.

Referring now to FIG. 4, in one example embodiment, the opening 16 may be ringed by the doped regions 40 and 42, the latter each being a sector of annulus centered about pore 14 and alternating with respect to the n- and p-doping. Inner edges of the regions 40 and 42 may be joined on a pair-wise basis by metallization layers 48 to provide one side of the Peltier device facing the opening 16. Different adjacent outer edges of each region 40 and 42 may also be joined by metallization layers 48 to provide a continuous circuit from one region 42' communicating at its outer edge with a contact 28 around the annulus to an adjacent region 40' communicating with contact 28'. Electrical voltage applied between contacts 28 and 28' will then establish a temperature gradient between the inside to the outside of the annulus moving heat from the opening 16 through the annulus into the liquid 22 with one polarity of current and moving heat from the liquid 22 toward the opening 16 with opposite polarity of current.

Figure 5:
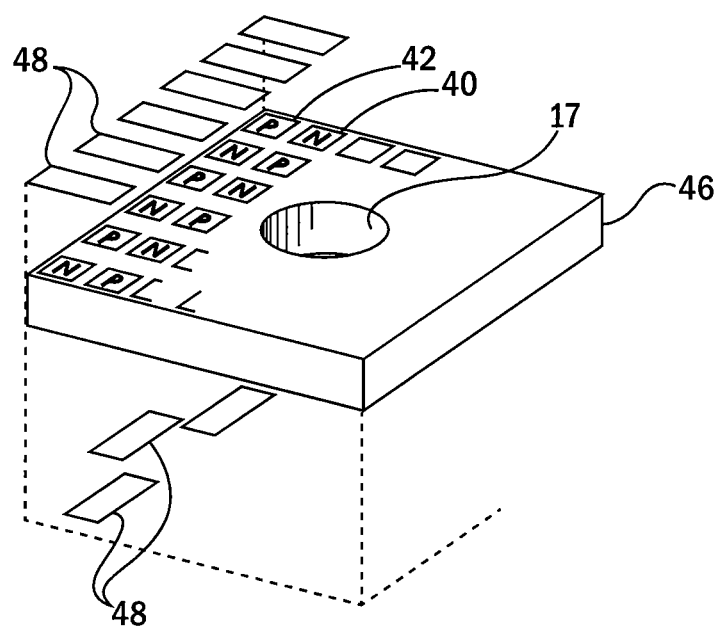
FIG. 5 is a perspective view of an alternative configuration of the doped regions establishing the Peltier device providing through-plane heat gradients.

Referring now to FIG. 5 in an alternative configuration, the regions 42 and 40 may be arranged in a checkerboard pattern and pairwise joined by metallization layers 48 on the top and bottom surfaces of the membrane 46, again providing a series connection of the regions 40 and 42. In this configuration a heat gradient is established through the plane of the membrane 46 rather than along the plane as would be the case in the configuration of FIG. 4.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A patch clamp chip for electrophysiology comprising:
   a substrate having an outer surface;
   a hole extending through the substrate and opening at the outer surface to provide a location adapted for immobilization of a cell membrane in an electrically sealing attachment against the opening; and
   a thermal element fixed to the outer surface proximate to the opening adapted to heat a cell membrane positioned on the opening according to a received electrical signal wherein the thermal element is a Peltier device and, wherein the thermal element is separated from a liquid by an insulating layer.

2. The patch clamp chip of claim 1 wherein the substrate is an insulating material.

3. The patch clamp chip of claim 2 wherein the substrate is selected from the group consisting of glasses and quartz.

4. The patch clamp chip of claim 1 wherein the hole is less than 1000 nanometers in diameter.

5. The patch clamp chip of claim 1 wherein the Peltier device is adapted to cool the cell membrane positioned on the opening according to a received electrical signal.

6. The patch clamp chip of claim 1 wherein the Peltier device is a semiconducting membrane having n- and p-doped regions.

7. The patch clamp chip of claim 6 wherein the semiconducting membrane is less than 100 micrometers in thickness.

8. The patch clamp chip of claim 1 wherein the opening provides an outward flaring crater at the outer surface.

9. The patch clamp chip of claim 1 wherein the opening has a diameter of less than 20 nm.

10. The patch clamp chip of claim 8 wherein the opening has a surface finish suitable for establishing a gigaohm seal with a cell membrane.

11. A method of fabricating a patch clamp chip for electrophysiology of a type having a substrate having an outer surface; a hole extending through the substrate and opening at the outer surface to provide a location adapted for immobilization of a cell membrane sealed against the opening; and a thermal element fixed to the outer surface proximate to the opening adapted to heat a cell membrane positioned on the opening according to a received electrical signal; the method comprising the steps of:
  (a) fabricating a silicon membrane having at least one aperture therethrough and having a Peltier device adjacent to the opening integrated into the silicon membrane to provide the thermal element;
  (b) bonding the silicon membrane to the substrate such that the location for immobilization is centered within the aperture in the silicon membrane; and
  (c) providing electrical contacts communicating with the Peltier device for an application of the electrical signal to control a temperature in a region of the aperture.

12. The method of claim 11 further including the step of fabricating the silicon membrane on a silicon substrate and then releasing the silicon membrane from the silicon substrate by selective etching.

13. The method of claim 12 further including the step of bonding the silicon membrane to the substrate before release from the silicon substrate by selective etching.

14. The method of claim 11 further including the step of fabricating the Peltier device by doping adjacent n- and p-regions and interconnecting them by metallization paths on an exposed surface of the silicon membrane after it has been bonded to the substrate and wherein the electrical contacts are metallization paths on the exposed surface of the silicon membrane.

15. The method of claim 11 wherein the step of doping adjacent n- and p-regions applies the regions in a pattern circling the aperture.

16. The method of claim 11 further including the step of forming the hole in the substrate by:
  (a) creating a multi-layered assembly comprising,
    (i) the substrate material; and
    (ii) an energy absorbing material being adjacent to one of the opposing outer surfaces so as to define an interface between the substrate and energy absorbing materials;
  (b) after creating the multi-layered assembly, applying a laser through the multi-layered assembly so that it passes into and has energy absorbed by the energy absorbing material; and
  (c) producing a shock wave at the interface to remove material from and create a hole through an entire thickness of the substrate material in a direction of propagation that begins at the interface and extends toward the outer surface of the substrate material that opposes the interface.

17. The method of claim 11 further including the steps of:
  (d) attaching a cell membrane over the opening;
  (e) performing electrical measurements of the electrical characteristics of the cell membrane while, applying a temperature gradient to the cell membrane through current passed through the Peltier device.

18. The method of claim 17 wherein the temperature gradient heats a region near the cell membrane with respect to a fluid surrounding the cell membrane.

19. The method of claim 18 wherein the temperature gradient cools a region near the cell membrane with respect to a fluid surrounding the cell membrane.

* * * * *